Figure 1:
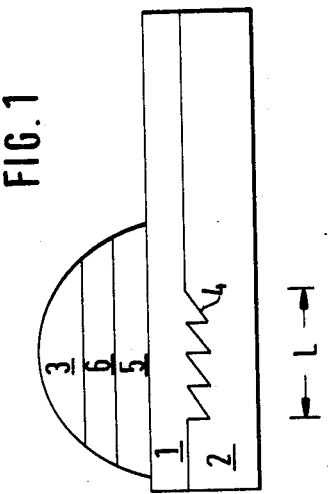

United States Patent [19]

Tiefenthaler et al.

[11] Patent Number: 4,815,843
[45] Date of Patent: Mar. 28, 1989

[54] OPTICAL SENSOR FOR SELECTIVE DETECTION OF SUBSTANCES AND/OR FOR THE DETECTION OF REFRACTIVE INDEX CHANGES IN GASEOUS, LIQUID, SOLID AND POROUS SAMPLES

[75] Inventors: Kurt Tiefenthaler, Zürich; Walter Lukosz, Greifensee, both of Switzerland

[73] Assignee: Oerlikon-Buhrle Holding AG, Zurich, Switzerland

[21] Appl. No.: 19,557

[22] PCT Filed: May 29, 1986

[86] PCT No.: PCT/CH86/00072

§ 371 Date: Jan. 27, 1987

§ 102(e) Date: Jan. 27, 1987

[87] PCT Pub. No.: WO86/07149

PCT Pub. Date: Dec. 4, 1986

[30] Foreign Application Priority Data

May 29, 1985 [CH] Switzerland .................. 2256/85
May 29, 1985 [CH] Switzerland .................. 2257/85

[51] Int. Cl.[4] ............... G01N 21/41; G01N 21/75; G01N 33/53
[52] U.S. Cl. ................. 356/128; 350/96.19; 350/136
[58] Field of Search ............... 356/128, 136; 350/96.15, 96.19

[56] References Cited

U.S. PATENT DOCUMENTS 3,856,404 12/1974 Hershler .................. 356/36
4,344,438 8/1982 Schultz .................. 128/634

FOREIGN PATENT DOCUMENTS 8100912 4/1981 PCT Int'l Appl.

OTHER PUBLICATIONS

Tiefenthaler et al. "Integrated optical switches and gas sensors", *Optics Letters* vol 10, No. 4 (Apr. 1984) pp. 137–139.

Chabay, I. "Optical Waveguides" *Analytical Chemistry*, vol. 54, No. 9 (Aug. 1982) pp. 1071A–1080A.

Lukosz et al "Embossing technique for fabricating integrated optical components in hard inorganic waveguide materials", Optics Letters, vol. 8, No. 10 (Oct. 1983) pp. 537–539.

Sutherland et al "Optical Detection of Antibody–Antigen Reactions at a Glass–Liquid Interface", *Clinical Chemistry*, vol 30, No. 9 (1984) pp. 1533–1538.

Primary Examiner—Richard A. Rosenberger
Attorney, Agent, or Firm—Ladas & Parry

[57] ABSTRACT

The optical sensor for the detection of specific substances and refractive index changes in gaseous, liquid, solid and porous samples is composed of integrated optical elements. It consists of a waveguiding film (1) equipped with a diffraction grating (4) and applied onto a substrate (2). For the selective detection of a specific substance contained in the sample (3) a selectively chemisorbing additional layer (5) covers the film (1) at least in the grating region. The sample (3) is applied at least in the grating region either directly onto the waveguiding film (1) or onto the selectively chemisorbing additional layer (5). Chemisorption of the substance, which is contained in the sample (3) and is to be detected, to the selectively chemisorbing additional layer (5) results in a further adlayer (6) coating the waveguiding film (1). The principle of the sensor is as follows: Due to chemisorption of a further adlayer (6) and/or due to a refractive index change of the sample (3) a change in the effective refractive index N of a mode guided in the waveguiding film (1) is effected. For the detection of this change the set-up (1,2,3,4,5) described above is used as grating coupler or Bragg reflector.

31 Claims, 3 Drawing Sheets

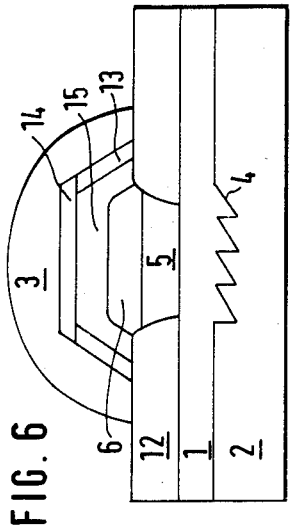
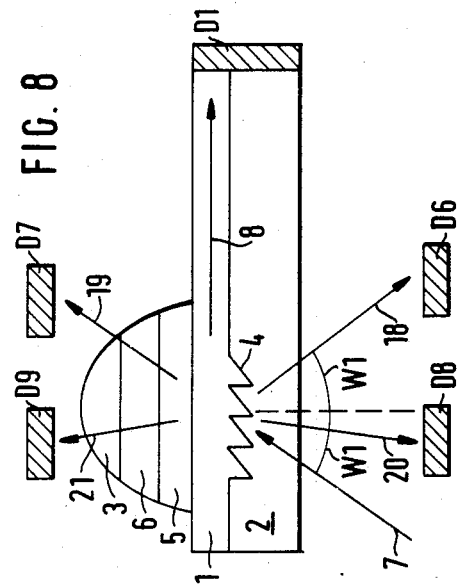
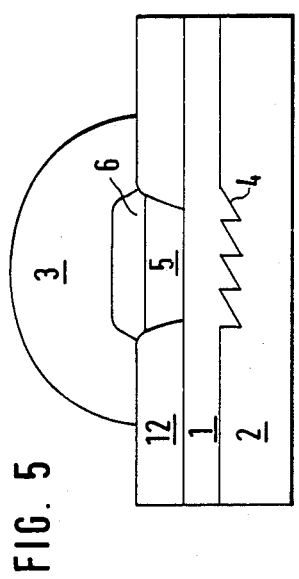
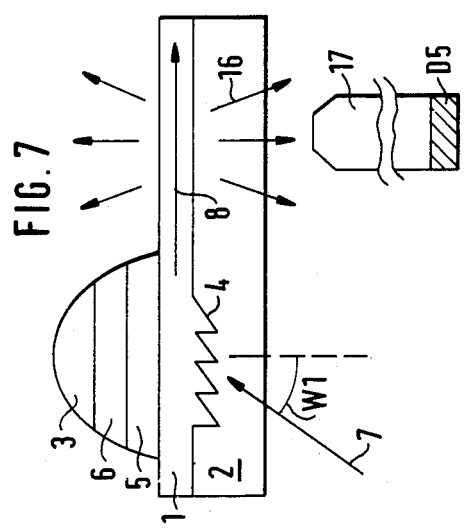

OPTICAL SENSOR FOR SELECTIVE DETECTION OF SUBSTANCES AND/OR FOR THE DETECTION OF REFRACTIVE INDEX CHANGES IN GASEOUS, LIQUID, SOLID AND POROUS SAMPLES

The present invention refers to an optical sensor according to the main patent claim. A well-known device for measuring refractive index changes in liquid, solids and porous samples is the refractometer which determines the angle of total internal reflexion between two media where the reference medium is a high index prism of known refractive index. A well-known device for the detection of chemisorbate layers and of chemically bound layers on surfaces in the ellipsometer analysing the state of polarisation of th elight being reflected at the chemisorbate layer (cf. R. Azzam et al., Physics in Medicine and Biology 22 (1977) 422–430; P. A. Cuypers et al., Analytical Biochemistry 84 (1978), 56–67), These devices are voluminous and the required sample volume is rather big what can be a great disadvantage in case of expensive samples. Furthermore the measurement accuracy of an ellipsometer is limited since the cell containing the liquid can influence the state of polarisation of the light. Another well-known instrument for the detection of adsorbed antigens, antibodies and haptens is the refractometer described in EP 0073980. A relatively new method for the detection of adsorbate layers is based on the excitation of surface plasmons at metal layer interfaces with or without using a diffraction grating (cf. B. Liedberg et al., Sensors and Actuators 4 (1983), 299 and EP 0112721). Thin metal films are not very stable and show ageing effects in their optical properties, what may be causing problems in practical applications.

The methods mostly used for the immunological determination of antibodies, antigens and haptens and for the determination of concentrations of metabolites such as glucose are based on the use of markers such as radioisotopes, enzymes or fluorescent tracers (EP 0103426, U.S. Pat. No. 4,344,438), which are chemically bound to a counter ligand, that is, to a complementary biomolecule. Sometimes, however, labeling leads to a perturbation of the binding behaviour of the corresponding biomolecule what means a decrease of the binding affinity.

Ellipsometry, reflectometry and excitation of surface plasmons allow a direct measurement of the immunological reaction (without using labels), but have the disadvantages mentioned above. Nephelometry is another direct measurement method but it is not very sensitive.

The invention as characterized in the claims solves the problem to provide an optical sensor which shows one or several of the following characteristic properties, namely (1) enabling a selective detection specific substances contained in gaseous, liquid, solid or porous samples (2) resolving changes in surface coverage of less than a hundredth of a monomolecular layer uids, solids or porous materials of less than $1.10^{-5}$ (4) distinguishing simultaneously and continuously between surface coverage and refractive index change (5) requiring very small sample volumes (6) requiring little space (7) working multifunctionally by integration of several detectors on a single chip.

Figure 2:
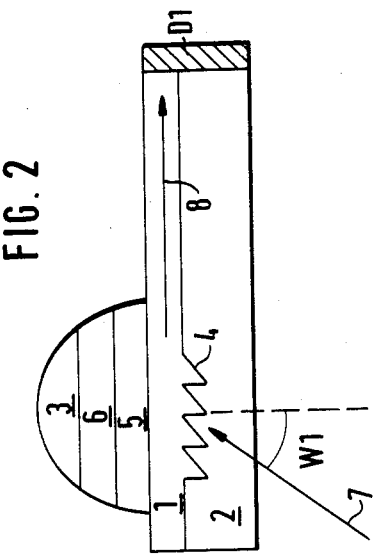
Figure 3:
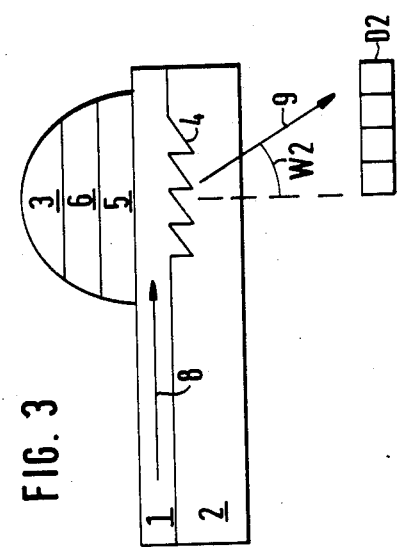
Figure 4:
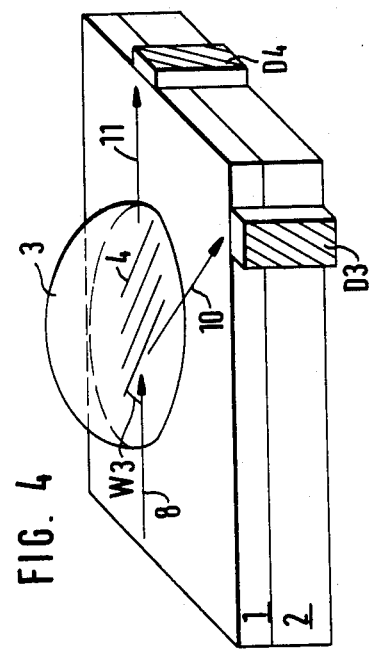

The invention will be now described by way of example with reference to the accompanying drawings in which FIG. 1 is a schematic diagram of the basic elements of the invention where a waveguiding structure located at the surface of a substrate and depicted in the subsequent drawings as a planar waveguiding film is provided with a diffraction grating and, optionally, with an additional layer FIG. 2 is in accordance with the invention a schematic view of a measuring device operating as an input grating coupler FIG. 3 is in accordance with the invention a schematic view of a measuring device operating as an output grating coupler FIG. 4 is in accordance with the invention a schematic view of a measuring device operating as a Bragg reflector FIG. 5 is an extended schematic diagram of the basic elements of the invention where outside the grating region the waveguiding structure is coverred by a protective layer FIG. 6 is an extended schematic diagram of the basic elements of the invention where a membrane optionally attached to a cell is located between the sample and the waveguiding structure with or without additional layer FIG. 7 is in accordance with the invention a schematic view of a device for indirect measurement of the intensity of a guided lightwave where the scattered light produced by the guided wave is collected by a fiber and sent to a detector FIG. 8 is in accordance with the invention a schematic view of a device for indirect measurement of the intensity of a guided lightwave where the intensity of one or several non-incoupled diffraction orders is measured.

Figure 9:
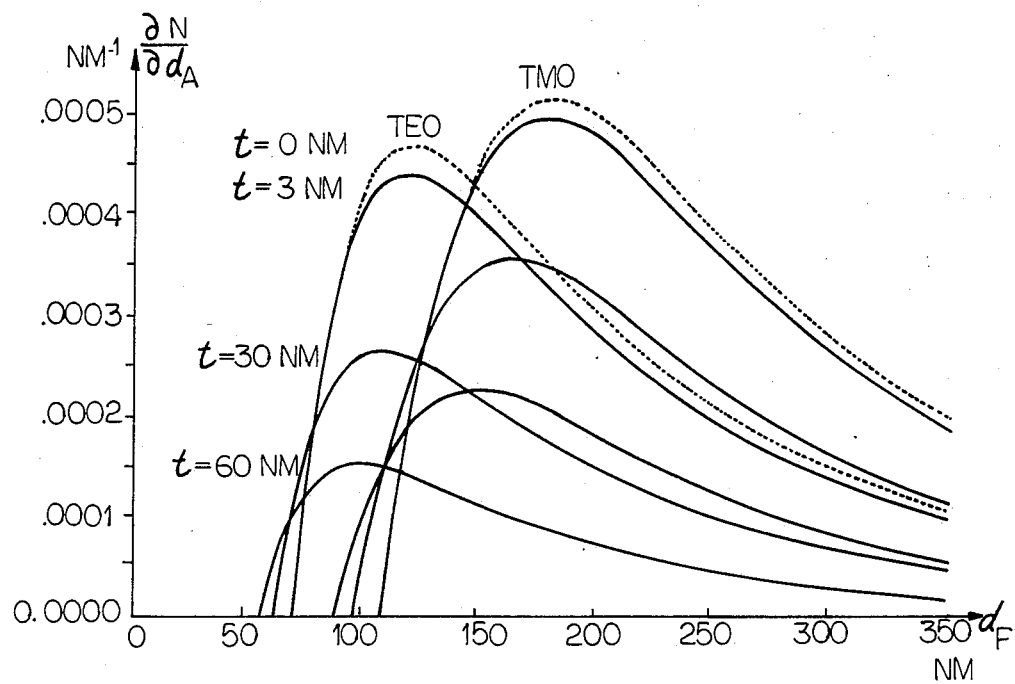

FIG. 9 is a chart showing the relationship between sensitivity of the sensor and the thickness of the chemo-responsive layer.

The basic component in integrated optics is the waveguiding structure, in particular the planar waveguide. It consists of a thin dielectric layer on a substrate. Incoupled laser light is guided in this thin layer by total internal reflexion. The propagation velocity of a guided lightwave (subsequently called "mode") is $c/N$, where c is the speed of light in vacuo and N the effective refractive index of the mode guided in the waveguide. The effective refractive index N is determined by the configuration of the waveguide (thickness and refractive index of the waveguiding film as well as refractive index of the substrate) and by the refractive index of the medium adjacent to the waveguiding film.

Waveguiding may occur not only in a thin planar layer but also in any other waveguiding structures, in particular in strip waveguides where the waveguiding structure has the form of a strip.

On top of the waveguiding film (or between waveguiding film and substrate) an additional layer may be applied without completely distroying the waveguiding properties of the multilayer system. For the operation of the sensor it is essential that a change of the refractive index of the medium adjacent to the waveguiding film (with or without additional layer) and/or a change of the refractive index (and/or of the optical absorption coefficient) and/or a change of the thickness of the waveguiding film itself or of an additional layer adjacent to the waveguiding film cause a change of the effective index N. These changes are caused by molecules of the substance to be detected through adsorption, desorption or chemisorption processes or through chemical reactions.

For the detection of refractive index changes of a sample it is applied directly to the waveguiding film (which is optionally covered by an additional layer) or optionally to an appropriate membrane preventing contaminantions, or in particular particles (contained in the sample), to get into contact with the waveguiding film.

Selective detection of a specific substance contained in the sample (e.g. certain biomolecules in liquid phase) is obtained by one of the two following measures or by a combination of them:

(1) Application of a membrane permeable only for the substance to be detected permits only this specific substance to get into contact with the waveguiding film (with or without additional layer)

(2) By appropriate choice of the additional layer it is attained that preferentially the substance to be detected physisorbs or chemisorbs in the volume or at the surface of the additional layer or causes chemical reactions and/or induces certain molecules of the additional layer to desorb.

The principle of the sensor is based on the fact that changes of the effective index can be detected by a diffraction greating operating as input grating coupler or output grating coupler or Bragg reflector. The operation of an input and output coupler and of a Bragg reflector is described in more detail in connection with the accompanying drawings.

FIG. 1 shows a schematic diagram of the basic elements of the invention. A thin layer forming a planar waveguiding film 1 covers a substrate 2 (e.g. a pyrex glass). The waveguide ½ consists of the waveguiding film 1 and the substrate 2. For instance the waveguiding film 1 is an oxide layer (such as $SiO_2$, $TiO_2$, $SnO_2$ or mixtures of these materials) or a polymer layer (such as polystyrole, polycarbonate etc.) or comprises two or more layers superimposed on top of each other. By using diffusion techniques, for instance, the surface of a substrate can be modified in such a way that the waveguiding film is formed immediately below the substrate surface. For the propagation of laser light in a waveguiding film 1 by total internal reflexion it is necessary that the refractive index of the waveguiding film 1 is higher than the index of the adjacent media (i.e. substrate 2 and sample 3). The waveguiding film 1 may have a microporous structure which for example can be produced when the waveguiding film is fabricated by a dip coating technique.

At either the interface waveguiding film 1/substrate 2 or waveguiding film 1/sample 3 or in the volume of the film 1 there is a diffraction grating 4 of length L. Surface relief gratings can be fabricated for instance by an embossing technique where the grating structure of a master is embossed either into the substrate 2 or the waveguiding film 1. Embossing into polymer layers or organometallic layers is described in literature (cf. R. Ulrich et al., Appl. Phys. Lett. 20 (1972), 213–215 and W. Lukosz and K. Tiefenthaler, Optics Lett. 8 (1983), 537–539).

In particular the embossing technique allows fabrication of surface relief gratings which show a spatially non-uniform modulation perpendicular to the grating lines although the master is a uniform modulated grating. This is obtained especially by laterally varying the emboosing pressure and by bending either the master grating or the substrate 2 (with or without waveguiding film 1). With the embossing technique described above it is possible to fabricate surface relief gratings consisting of two strongly modulated grating regions separated by a weakly modulated region. Thereby the master grating is pressed against the substrate 2 (with or without waveguiding film 1) by applying two locally separated but parallel knife-edges.

The diffraction grating 4 is employed for either coupling an incident laser beam into the waveguiding film 1 or for coupling a guided mode out of the waveguide or for partly transmitting and partly reflecting a guided mode entering the grating region.

Optionally the waveguiding film 1 is covered at least in the grating region by an additional or chemoresponsive layer 5 which allows selective detection of a specific substance contained in the sample 3. The sample to be examined is applied to the additional layer 5 or to the waveguiding film 1, respectively, at least in the grating region.

When the optical sensor is working exclusively as integrated optical (differential) refractomer (i.e. when only refractive index changes occurring in the sample 3 are measured) the additional layer 5 is omitted or it is of such nature preventing adsorption of molecules contained in the sample 3. For instance no polar substance adsorb to ODS (octadecylsilane) or to surfaces showing any alkyl groups. As an example water cannot wet non-polar (hydrophobic) alkyl groups. Reversed-phase-chromatography is using this fact extensively (cf. V. Meyer, Laborbücher Chemie: Praxis der Hochleistungs-Flüssigchromatographie). Refractive index changes of a liquid sample 3 can be caused for instance by a (bio)chemical reaction occurring in the sample 3. But the sample 3 can also consist of a solid or porous material.

For a selective detection the additional layer 5 or the waveguiding structure 1 have to be chosen such that they selectively chemisorb or chemically bind only a specific substance contained in the sample 3. Then the chemisorbate forms a further layer 6.

Furthermore this principle of selectivity of the optical sensor can be used in immunology to identify antigen-antibody complexes. As an example the additional layer 5 consists of molcules of a certain antigen. Then coupling between antigen and antibody can only take place when the corresponding antibody is contained in the sample 3. In this example the chemisorbed layer 6 consists of antibody molecules. The degree of coverage of the chemisorbed layer 6 depends on the antibody concentration in the sample 3 as well as on the time of incubation. Thus the present optical sensor can be applied to the determination of antibody concentrations by measuring the maximum degree of coverage or the stationary degree of coverage being established after a certain time.

The organisation and regulation of all biological systems is guaranteed by the selective recognition of biomolecules via the lock-and-key principle. Therefore this principle can also be applied to biosensorics. Besides antigens and antibodies also other pairs of biomolecules show complementary behaviour such as haptens and antibodies, enzymes and enzyme inhibitors, hormones or neurotransmitters and receptors, or complementary nucleic acids. All these kinds of complementarity can be used as selectivity principle for the optical sensor where one of the two complementary biomolecules is immobilized on the waveguiding film 1 and thus forms the additional layer 5. The other biomolecule forms the layer 6.

In case of reversible binding of a specific substance to the receptor the surface coverage, i.e. the thickness of the layer 6, depends in equilibrium on the concentration of the specific substance dissolved in the sample 3. By decreasing the concentration of this substance in the sample 3 the molecules of this substance reversibly bound to the receptor molecules start to desorb from the surface to the sample 3 until equilibrium is established again. Desorption means reduction of the thickness of the layer 6.

The lock-and-key principle can also be used in a more elaborated way. Well-known is the so-called sandwich method where the lock-and-key principle is carried out repeatedly (example: antibody-antigen-antibody complex formation). Well-known is also the so-called competition method where two different species of biomolecules mostly of different molecular weight compete for the same binding sites at the receptor molecules (i.e. at the additional layer 5). When the concentration of one species of molecules contained in the sample 3 is increased the other species of molecules is partially expelled from the binding sites of the receptor molecules (EP 0073980). This desorption leads to a detectable change in thickness of layer 6. Thus the thickness change is a measure for the concentration of the species of molecules to be detected. A further possibility of concentration measurement lies in the observation of the dynamical behaviour of the adsorption or binding process. The thickness change of layer 6 as function of time or the velocity of growth of layer 6, respectively, determine the concentration of the specific substance to be detected (cf. G. Traexler, Medizintechnik 99 (1979), 79–84, J. C. Sternberg, Clin. Chem. 1456 (1977).

The surface of the waveguiding film 1 may be pretreated before immobilizing the receptor molecules. As an example a thin polymer film (e.g. made up of polystyrole) may cover the waveguiding film 1 in order to improve adhesion of the receptor molecules. Instead of polymer films also oxide layers can be used. Preferably such oxide materials are used which are also applied in (adsorption) chromatography as so-called stationary phase. With or without chemical activation of the oxide layer the receptor molecules are immobilized after known recipes. When the waveguiding film 1 itself is made up of an oxide material the deposition of a polymer or supplementary oxide film can be omitted under certain circumstances. Improved immobilization can be obtained additionally when the oxide layer or the waveguiding film 1, respectively, is treated with reactive silanes.

The substance which is selectively chemisorbing or chemically binding may form an additional layer 5 and/or may be partially or completely filling the micropores of the waveguiding film 1. In the latter case chemisorption or chemical binding takes place in the waveguiding film 1 itself.

The additional layer 5 may also show the unique property that it allows only the specific substance which is to be detected and is contained in the sample 3 to penetrate into the additional layer 5. In this case the additional layer 5 has a high solubility for the substance to be detected. This way of achieving selectivity is known for a long time and is applied for piezoelectric quartz crystal detection (cf. U.S. Pat. No. 3,164,004). For instance a silicone oil film has a high solubility for hydrocarbons. Adsorption of hydrocarbons to the silicone oil film covering the quartz crystal causes a change in the oscillation frequency of the crystal (cf. A. Kindlund and I. Lundstroem, Sensors and Actuators 3 (1982/83), 63–77). In the present invention the additional layer 5 may consist e.g. of such a silicone oil film.

Chemical reactions which are induced in the additional layer 5 or in the waveguiding film 1 itself by the substance to be detected may also lead to a change of the refractive index and/or the light absorption coefficient (imaginary part of the refractive index) and/or the film thickness of the corresponding layer (cf. E. E. Hardy et al., Nature 257 (1975), 666–667 and C. Nylander et al., Sensors and Actuators 3 (1982/83), 79–88). But also chemical reactions occurring in the sample 3 itself may, besides effecting a refractive index change, lead to a change of the light absorption coefficient (e.g. colour change) of the sample 3. All effects cause a change of the effective index N which becomes a complex number when a light absorption coefficient different from zero is induced.

Referring to FIG. 2 a lazer beam 7 is coupled into the waveguide $\frac{1}{2}$ by a diffraction grating 4 and propagates in the waveguide $\frac{1}{2}$ as a guided lightwave. The laser beam 7 is incident onto the grating 4 from either the sample side or advantageously from the substrate side. As a laser, for instance, a helium-neon laser, a cw or pulsed laser diode or instead of a laser a light-emitting diode (LED) both with corresponding collimation optics are used. The incoupling condition has the character of a resonance condition. The well-defined angle of incidence W1 of the laser beam 7, at which maximum intensity of the guided mode 8 is obtained, depends on the effective index N. The effective index N of the guided mode 8 is determined by the refractive indices of the media forming the waveguide $\frac{1}{2}$, the refractive index of the sample 3, the thickness of the waveguiding film 1 and the refractive index and thickness of both the selectively chemisorbing additional layer 5 and the chemisorbate layer 6. When the effective index N of the guided mode 8 is changed by influence of the sample 3, the angle of incidence Q1 originally chosen is not any more the optimum one which causes a change of intensity of the guided mode 8. The change in effective index N can be measured by different methods.

For small effective index changes the change in light intensity of the guided mode 8 can be measured by the detector D1 at constant angle of incidence Q1 and constant wavelength, from which the change of effective index is determined. This measuring method is applicable for measurements of effective index changes which are smaller than the half width of the resonance incoupling curve. The incoupling curve shows the character of a resonance both with respect to the angle of incidence W1 and the effective index N. The half width of the resonance incoupling curve depends on the length L of the grating due to diffraction (cf. K. Tiefenthaler and W. Lukosz, Optics Letters 9 (1984), 137–139). For instance, with a grating of length L=6 mm and a wavelength of 633 nm the optical sensor is able to resolve changes in surface coverage of a hundredth of a monomolecular layer, e.g. of a $H_2O$ monolayer, and/or refractive index changes of the sample 3 in the order of $10^{-5}$, provided that intensity changes of the guided mode can be measured with a resolution of 1%.

For effective index changes which are greater than the half width of the resonance incoupling curve the light intensity of a guided mode 8 is measured and the incoupling angle W1 of the laser beam 7 is adjusted in such a way that the light intensity is always at its maximum value or is at least constant. From a change of the angle W1 the change of the effective index can be determined. There exists also the possibility to choose the angle W1 in such a way that a guided mode 8 attains its maximum intensity when the thickness of chemisorbate layer 6 and/or the refractive index change of the sample 3 assume a desired value.

A further measuring method makes use of the relation between the angle of incidence W1, at which optimum incoupling occurs, and the laser wavelength. In this measuring method the angle of incidence W1 remains constant and the wavelength of a tunable laser is changed in such a way that the intensity of the guided mode 8 maintains its maximum or, respectively, a constant value, while the effective index is changed by the influence of the sample 3. From the change of wavelength the change of the effective index is determined.

FIG. 3 shows in accordance with the invention the measuring device used as an output grating coupler. Waveguide 1, diffraction grating 4 and selectively chemisorbing additional layer 5 are described in the context of FIG. 1. When a guided mode 8 falls on the diffraction grating 4 the laser light is partially or completely coupled out. The outcoupled laser beam 9 leaves the waveguide 1 for a constant wavelength under a certain angle W2 which is determined by the effective index. Excitation of the guided mode 8 is not shown in FIG. 3. For example, the guided mode can be excited by endfire coupling, prism coupling, grating coupling etc. (cf. T. Tamir, Integrated Optics, Chap. 3). A change of the effective index induced by the sample 3 in the grating region leads to a change of the outcoupling angle W2. This change in angle can for example be measured by a photodiode array or a position dependent photodetector D2. For small angle changes of the outcoupled laser beam 9 it is also possible to measure the change of intensity of the outcoupled laser beam 9 incident onto a detector D2 having a smaller detection area than the beam diameter area since the outcoupled laser beam 9 moves across the detector D2 during the measuring procedure. From the change of angle or the change of intensity, respectively, the change of effective index is determined.

By a suitable choice of the wavelength of a tunable laser the outcoupling angle W2 could be kept constant while the influence of sample 3 leads to a change of the effective index. From the change of wavelength the change of effective index can be determined.

In FIG. 4 a so-called Bragg reflector is shown. For reasonsof space the selectively chemisobing additional layer 5 and the layer 6 are omitted in FIG. 4. The diffraction gratings used as grating couplers (FIGS. 2 and 3) can also be used as Bragg reflectors. A guided mode 8 is Bragg reflected at the diffraction grating 4 if the Bragg condition is fulfilled, i.e. the angle W3 is identical with the Bragg angle (cf. W. Lukosz and K. Tiefenthaler, Optics Letters 8 (1983), 537–539). The excitation of the guided mode 8 is described in the context of FIG. 3. The detectors D3 and D4 measure the intensities of the reflected mode 10 and of the transmitted mode 11. The Bragg angle W3 is determined by the effective index N in the grating region.

When the effective index N is changed by the influence of the sample 3 the Bragg condition is perturbed. Consequently the intensities of the reflected and transmitted mode are changed. From the light intensities of the reflected mode 10 and/or transmitted mode 11 measured by the detectors D3 and/or D4 the change of the effective index is determined.

It is also possible to adjust the angle W3 in such a way that the Bragg condition is not satisfied leading to a missing reflected mode 10. When the effective index change assumes a desired value a reflected mode 10 appears since the Bragg condition is now satisfied.

Another method of measurement takes advantage of the wavelength dependence of the Bragg condition. Although the effective index is changed by the influence of the sample 3 the Bragg condition can remain satisfied by choice of the suitable laser wavelength. From the change of wavelength the change of the effective index is determined.

In particular the Bragg reflector can be operated with an angle W3 of 90 degrees. In this case the guided mode is retroreflected. It is an advantage of the retro-reflector that the reflected mode maintains its original width and does not fan out. Instead of a planar waveguide also a strip waveguide could be used.

As the Bragg reflector the diffraction grating with non-uniform modulation as described in FIG. 1 can be employed, inparticular a diffraction grating having two strongly modulated grating regions separated from each other by a weakly modulated region. The additional layer 5 may only cover the weakly modulated grating region. These special gratings described can be used not only as Bragg reflector but also as input and output grating coupler. When this special grating is employed as output coupler an interference fringe pattern is observed on the detector D2 in FIG. 3. When this grating is used as input grating coupler the incoupling efficiency as function of the effective index N or the angle of incidence W1 shows several maxima and minima. When this grating is used as a Bragg reflector is transmittance and reflectance have several maxima and minima as functions of the effective index.

In FIGS. 1–8 the waveguiding film 1 is shown as a planar structure. However, also other structures exist in which waveguiding is possible. For example instead of a planar waveguide a strip waveguide can be used. In this case the waveguiding film 1 forms a strip which can be either on the top of the substrate or within the substrate (but near the surface). The refractive index of the strip is higher than the indices of the surrounding materials. The mode 8 is then guided in both space coordinates perpendicular to the direction of mode propagation by total internal reflexion.

By light scattering or light absorption induced by the sample 3 and/or by adsorbed macromolecules, e.g. proteins, the guided mode may be attenuated so strongly after leaving the grating region that a measurement of the light intensity may become impossible. In order to prevent this disturbing effect it is advantageous to cover the waveguiding film 1 outside the grating region with a protective layer 12 (see FIG. 5). This protective layer 12 has to have a low refractive index; it can e.g. be an $SiO_2$ layer. The thickness of the protective layer 12 has to be chosen big enough so that an interaction between the guided mode and the sample 3 is prevented outside the grating region, because of a sufficient decrease of the evanescent field of the mode. But the protective layer 12 also helps to prevent perturbation of the mode induced by the cell 13 (shown in FIG. 6).

FIG. 6 shows a modified version of the sensor described in FIG. 5; it incorporates a membrane which improves both selectivity and stability of the sensor.

The membrane 14 permits only a "filtered" sample 15 to get into contact with the waveguiding structure 1 or the additional layer 5, respectively, so that in the "filtered" sample 15—besides a solvent or buffer solution—only the specific substance to be detected is present. The sample 3 is applied to a membrane 14 optionally supported by a cell 13, the membrane permits only the substance contained in the sample 3 which is to be detected to permeate, while the remaining substances not being of interest are kept back.

If the selectivity of a membrane is high enough the additional layer 5 could be omitted. In this case unspecific adsorption or chemisorption takes place at the waveguiding structure 1. Sample 3 and "filtered" sample 15 can be either liquid or gaseous.

It is also possible to cover the waveguiding film 1 or the additional layer 5 directly by a (biological) membrane. The receptor molecules may form an additional layer 5 or may be implanted into the membrane.

If durable membranes, e.g. glass membranes, are used they can also serve as substrate. In this case the membrane is covered by a waveguiding film 1 or optionally first coated with an additional layer 5 and then with the waveguiding film. The sample is applied to the membrane substrate.

In FIGS. 2 and 4 detectors are shown which measure directly the intensity of the guided modes 8 or 10 and 11, respectively. But it is also possible first to couple out a guided mode for example by a second grating and then to measure the intensity of the outcoupled laser beam by a detector. This intensity is proportional to the intensity of the guided mode. The outcoupling mechanism of the second grating must not be disturbed by the sample 3. This is achieved for instance by applying a protective layer in the region of the second grating in order to separate the sample 3 from the waveguide, or by not having any sample 3 in the region of this second grating (for description of the protective layer see context of FIG. 5). Outcoupling can also be accomplished by a prism coupler or a taper (cf. T. Tamir, Integrated Optics, Chap. 3).

In FIG. 7 a further detection scheme is described. In contrast to the diagram according to FIG. 2 the intensity of the guided mode 8 is not measured directly but the scattered light 16 of the mode 8 is collected by a fiber optics 17 leading to the detector D5. The intensity of the scattered light 16 is proportional to the intensity of the mode 8. The scattered light 16 is produced by inhomogeneities always existing in the waveguide 1. In case of a Bragg reflector the intensity of the scattered light of the reflected mode 10 and/or the transmitted mode 11 can be measured in the same way instead of a direct measurement.

In FIG. 8 a further indirect detection scheme is depicted. If a laser beam 7 is incident onto a diffraction grating 4 different diffraction orders are produced both in reflection and transmission. By properly choosing the angle W1 the laser beam 7 is coupled into the waveguiding film 1 via one and only one diffraction order. According to the law of energy conservation the incoupled power is missing in the remaining diffraction orders. But theory and experiment show that under certain conditions amplification of intensity may occur in certain non-incoupled diffraction orders when a guided mode is excited. Therefore changes of intensity of the guided mode 8 can be measured indirectly by measuring changes of intensity of one or several non-incoupled diffraction orders 18–21 with the detectors D6–D9. In FIG. 8 the reflected beam 18 is the zero diffraction order in reflection, the transmitted beam 19 the zero diffraction order in transmission, i.e. the light passing without diffraction. The beams 20 and 21 are diffracted beams of higher order in reflexion and transmission, respectively. In case of a Bragg reflector (see FIG. 4) there exist—beside the modes 10 and 11—under certain conditions also other diffraction orders which correspond to outcoupled beams the intensity of which is easily measurable.

The sensitivity of the integrated optical sensor is especially high when for a given sample 3 the change of effective index is especially high. Theory shows that especially high sensitivities are obtained when the refractive index of the waveguiding film 1 is much higher than the indices of the substrate 2 and the sample 3 and when the thickness of the waveguiding film 1 is slightly higher than the minimum thickness (so-called cut-off thickness). A minimum thickness of the waveguiding film 1 is necessary for excitation of a guided mode (cf. T. Tamir, Integrated Optics, Springer, Berlin 1979, Chap. 2). For obtaining high sensitivities the refractive index of the waveguiding film 1 has to be at least 1% but preferably more than 10% higher than the indices of the substrate 2 and the sample 3. However, if index changes in a sample 3 are to be measured, the refractive index of which is higher than that of the substrate 2, a high index difference between waveguiding film 1 and substrate 2 (or sample 3), is not required to achieve a high sensitivity.

If the sensitivities are known from theory either the state of the adsorption or desorption process (especially the thickness change of the chemisorbate layer 6) or the refractive index change of the sample 3 can be determined.

If both the thickness change of the chemisorbate layer 6 and the refractive index change of the sample 3 are to be determined then the effective index changes of two different modes have to be measured simultaneously. In the case where the field of the guided mode is evanescent in the adsorbate layer 6 the thickness of the layer 6 has to be smaller than the so-called penetration depth in order that refractive index changes of the sample 3 can be measured.

In FIG. 9, a chart shows the relationship between the sensitivity of the sensor and the thickness of the chemoresponsive layer. In the chart, t denotes the thickness of the chemo-responsive layer that covers the waveguiding film, $d_F$ denotes the thickness of the waveguiding film and $d_A$ denotes the thickness of the adsorbate layer. It should be noted that the chemo-responsive layer is a protein layer and that the refractive index is 1.4.

For simultaneous excitation of two different modes of same wavelength by an input grating coupler (see FIG. 2) two laser beams have to be simultaneously incident onto the diffraction grating 4 at two different angles of incidence. This can be accomplished even with one laser by using a appropriate beam splitting device.

Simultaneous measurement of intensity changes of two different modes can be effected either via non-incoupled diffraction orders or via beams outcoupled by an output coupler since non-incoupled or outcoupled beams corresponding to different modes propagate in different directions and therefore can be detected separately.

However, when exact simultaneousness of the two intensity measurements is not required, a direct measurement of intensity of the two modes can be performed at the end of the waveguide ½ by a multiplex procedure, by blocking alternately the two incident laser beams exciting the two different guided modes. In case of slow processes it is permissible to excite the two guided modes successively with only one incident laser beam by adjusting and measuring successively the corresponding angles of incidence.

It is also possible for instance to choose both angles of incidence in such a way that the two different guided modes propagate in the waveguide ½ in opposite directions. Thus the two changes of intensity can be measured directly and simultaneously by two spatially separated detectors.

Simultaneous measurement of effective index changes of two different guided modes may also be performed with only one incident laser beam which consists of two suitable different wavelengths. In this case the two different modes differing also in wavelength can be incoupled with one angle of incidence.

When both a thickness change of the chemisorbate layer 6 and a refractive index change of the sample 3 have to be measured by an output grating coupler or a Bragg reflector two different guided modes have to be simultaneously coupled out of the waveguide ½ or Bragg reflected at the grating 4.

In intensity measurements a high signal-to-noise ratio is desired for achieving high measurement accuracies. Fluctuations of laser power reduce the measurement accuracy. This effect can be eliminated by dividing the incident laser beam (somewhere in front of the diffraction grating 4) with a beam splitter; thus producing a reference beam the intensity of which is measured by a reference detector. The ratio of the intensities of the signal and the reference beam is independent of the laser power fluctuations.

The signal-to-noise ratio can also be improved by using well-known lock-in techniques. In this technique the laser light incident onto the diffraction grating 4 is modulated. This is obtained by either modulating the light of a cw-laser with a chopper or using a pulsed laser diode or light emitting diode (LED) as a light source.

For getting a good signal-to-noise ratio it is furthermore necessary that the light spot on the diffraction grating 4 (i.e., for instance in case of the input grating coupler, the spot illuminated by the laser beam 7) is spatially stable. This is achieved by choosing a laser with a high beam pointing stability and by mounting the laser very close to the diffraction grating. A further possibility is to insert a lens between laser and diffraction grating 4 which forms an image of the beam waist on the grating 4. The beam pointing stability also influences the precision of the angle of incidence W1. Use of lasers with high beam pointing stability increase the measurement accuracy of the optical sensor since the angle of incidence W1 is defined more precisely.

Since the electromagnetic field of the guided wave interacts as an evanescent wave with the sample 3 and therefore penetrates for less than a wavelength into the sample 3 the optical sensor allows refractive index change measurements of very small sample volumes. If the diffraction grating is illuminated over the whole distance L=2 mm and if the illumination spot has a width of 0.1 mm parallel to the grating lines the minimum sample volume is V=2 mm*0.1 mm*500 nm=0.1 nanoliter for a wavelength of about 500 nm.

Since the optical sensor reacts very sensitively both to refractive index changes of the sample 3 and to adsorption of specific molecules contained in the sample 3 and since the minimum sample volume is very small the application of the optical sensor as a detector for instance in liquid, gas and affinity chromatography seems promising.

Since the optical sensor consists of only few (passive) elements integrated on one substrate cheap fabrication seems feasible. Also for this reason it can be applied as a one-way sensor, for example, in biosensorics and medical diagnostics.

A further advantage of the present optical sensor lies in the possibility to integrate different optical sensors on one substrate. These sensor elements may have different additional layers 5 and/or membranes 14 and thus are selectively sensitive to different substances. These different sensor elements can be scanned by one laser either simultaneously or succesively.

We claim:

1. An optical sensor for detecting chemical, biochemical or biological substances in a sample, comprising:
    a waveguiding structure formed by a waveguiding film covering a substrate, wherein the waveguiding film has a refractive index at least 1% higher than the refractive index of the substrate;
    a diffraction grating contained in the waveguiding structure; and
    a chemo-responsive layer covering the waveguiding film in a region around the diffraction grating, wherein said chemo-responsive layer is capable of binding with the substances to be assayed and has a thickness of less than one wavelength.

2. An optical sensor according to claim 1, wherein the waveguiding structure outside the region around the diffraction grating is covered by a protective layer.

3. An optical sensor, according to claim 2, wherein the protective layer consists of $SiO_2$.

4. An optical sensor according to claim 3, wherein the protective layer tapers near the region around the diffraction grating.

5. An optical sensor according to claim 4, wherein the diffraction grating is a surface relief grating on the waveguiding structure.

6. An optical sensor according to claim 5, wherein the diffraction grating is a phase volume grating.

7. An optical sensor according to claim 6, wherein the waveguiding structure is a high index monomode structure.

8. An optical sensor according to claim 7, wherein the waveguiding film is covered by a binding layer.

9. An optical sensor according to claim 8, wherein the binding layer is a silane.

10. An optical sensor according to claim 9, wherein the chemo-responsive layer is a monomolecular layer.

11. An optical sensor according to claim 9, wherein the waveguiding structure is microporous in the region around the diffraction grating and the chemoresponsive molecules are brought into the micropores.

12. An optical sensor according to claim 11, wherein the substrate is microporous in the region around the diffraction grating and chemo-responsive molecules are brought into the micropores.

13. An optical sensor according to claim 11, wherein the chemo-responsive layer is composed of molecules of a specifically binding biological receptor that specifically blinds with biomolecules which are complementary to the receptor.

14. An optical sensor according to claim 13, wherein the chemo-responsive layer comprises antibodies for an antigen which is to be assayed.

15. An optical sensor according to claim 14, wherein a membrane of selective permeability is fixed on the protective layer.

16. An optical sensor according to claim 8, wherein the binding layer is a polymer.

17. An optical sensor according to claim 16, wherein the chemo-responsive layer is a monomolecular layer.

18. An optical sensor according to claim 16, wherein the waveguiding structure is microporous in the region around the diffraction and chemo-responsive molecules are brought into the micropores.

19. An optical sensor according to claim 18, wherein the substrate is microporous in the region around the diffraction grating and chemo-responsive molecules are brought into the micropores.

20. An optical sensor according to claim 18, wherein the chemo-responsive layer is composed of molecules of a specifically binding biological receptor that specifically binds biomolecules which are complementary to the receptor.

21. An optical sensor according to claim 20, wherein the chemo-responsive layer comprises antibodies for an antigen which is to be assayed.

22. An optical sensor according to claim 21, wherein a membrane of selective permeability is fixed on the protective layer.

23. A method for detecting chemical, biochemical or biological substances in a sample including the steps of:
measuring the effective index of an optical sensor comprising a waveguiding structure formed by a waveguiding film covering a substrate wherein the waveguiding film has a refractive index at least 1% higher than the refractive index of the substrate,
a diffraction grating in said waveguiding structure, and a chemo-responsive layer covering the waveguiding film in a region around the diffraction grating so that the chemo-responsive layer is capable of binding the substances to be assayed and has a thickness of less than one wavelength; contacting said optical sensor with the sample; and measuring the effective index change caused by the binding of the species to the chemo-responsive layer.

24. A method according to claim 23, wherein the maximum effective index change is measured in order to determine the concentration of the substances.

25. A method according to claim 24, in which the velocity of the effective index change is measured.

26. A method according to claim 25, wherein a laser beam is coupled into the waveguiding structure under a constant angle of incidence and the intensity change of the incoupled mode is measured.

27. A method according to claim 25, wherein a laser beam is coupled into the waveguiding structure under a constant angle of incidence and the intensity change of the non-incoupled diffraction order is measured.

28. A method according to claim 25, wherein a laser beam is coupled into the waveguiding structure under the angle of incidence leading to the highest intensity of the incoupled mode and measuring the effective index change by determining the change of the angle of incidence leading to highest intensity of the incoupled mode.

29. A method according to claim 25, wherein a laser beam is coupled into the waveguiding structure under a constant angle of incidence and the intensity change of the non-incoupled diffraction order is measured.

30. A method according to claim 25, wherein a laser beam is coupled into the waveguiding structure under a constant angle of incidence and the change of wavelength is measured.

31. A method according to claim 25, wherein a laser beam is coupled into the waveguiding structure and the change of the outcoupling angle is measured.

* * * * *

UNITED STATES PATENT AND TRADEMARK OFFICE
CERTIFICATE OF CORRECTION

PATENT NO. : 4,815,843
DATED : March 28, 1989
INVENTOR(S) : Kurt Tiefenthaler, Walter Lukosz It is certified that error appears in the above-identified patent and that said Letters Patent is hereby corrected as shown below:

Column 6,

Line 21, "lazer" should read --laser--

Column 6,

Line 41, "Q1" should read --W1--

Column 6,

Line 47, "Q1" should read --W1--

Signed and Sealed this

Thirtieth Day of April, 1991

*Attest:*

HARRY F. MANBECK, JR.

*Attesting Officer*  *Commissioner of Patents and Trademarks*